United States Patent
Nagae

(10) Patent No.: US 9,442,187 B2
(45) Date of Patent: Sep. 13, 2016

(54) OBJECT INFORMATION OBTAINING APPARATUS, DISPLAY METHOD, AND STORAGE MEDIUM

(71) Applicant: CANON KABUSHIKI KAISHA, Tokyo (JP)

(72) Inventor: Kenichi Nagae, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 480 days.

(21) Appl. No.: 13/975,099

(22) Filed: Aug. 23, 2013

(65) Prior Publication Data

US 2014/0064022 A1    Mar. 6, 2014

(30) Foreign Application Priority Data

Aug. 28, 2012  (JP) .................................. 2012-187617
Jul. 30, 2013  (JP) .................................. 2013-157608

(51) Int. Cl.
   *G03B 42/06*  (2006.01)
   *G01S 7/52*   (2006.01)
   (Continued)

(52) U.S. Cl.
   CPC ........ *G01S 7/52046* (2013.01); *G01S 7/52047* (2013.01); *G01S 7/52063* (2013.01); *G01S 7/52074* (2013.01); *G01S 15/8915* (2013.01); *A61B 8/463* (2013.01); *A61B 8/5207* (2013.01)

(58) Field of Classification Search
   CPC ........... G01S 7/52063; G01S 7/52074; G01S 15/8915; A61B 8/463; A61B 8/5207
   USPC .......................................................... 367/11
   See application file for complete search history.

(56) References Cited

U.S. PATENT DOCUMENTS

2002/0028994 A1  3/2002  Kamiyama
2007/0255136 A1  11/2007  Kristofferson et al.
(Continued)

FOREIGN PATENT DOCUMENTS

CN   101053521 A   10/2007
CN   102341723 A   2/2012
(Continued)

OTHER PUBLICATIONS

Magali Sasso and Claude Cohen-Bacrie, Medical Ultrasound Imaging using the Fully Adaptive Beamformer, IEEE International Conference on Acoustics, Speech, and Signal Processing, 2005, Proceedings, ICASSP '05, Mar. 18-23, 2005, Philadelphia, PA, vol. 2, pp. 489-492, IEEE, Piscataway NJ, 2005.

(Continued)

*Primary Examiner* — Mark Hellner
(74) *Attorney, Agent, or Firm* — Canon U.S.A. Inc., IP Division

(57) ABSTRACT

An object information obtaining apparatus according to the present invention includes a fixed signal processing unit configured to perform addition processing with a predetermined weight by using a plurality of receiving signals to obtain first distribution information, and an adaptive signal processing unit configured to perform adaptive signal processing with a weight adaptively changing according to the receiving signals by using the plurality of receiving signals to obtain second distribution information, wherein the display control unit, upon reception of information about a specified area in the image of the first distribution information input by the user in a state where the image of the first distribution information is displayed, is configured to output image information for displaying on the display unit an image of the second distribution information or the combined image for the first and second distribution information, corresponding to the specified area.

25 Claims, 7 Drawing Sheets

(51) Int. Cl.
*G01S 15/89* (2006.01)
*A61B 8/00* (2006.01)
*A61B 8/08* (2006.01)

(56) References Cited

U.S. PATENT DOCUMENTS

| | | | | |
|---|---|---|---|---|
| 2008/0167557 | A1* | 7/2008 | Kozai | A61B 8/06 600/441 |
| 2009/0299184 | A1 | 12/2009 | Walker et al. | |
| 2010/0106017 | A1 | 4/2010 | Shin et al. | |
| 2011/0306884 | A1 | 12/2011 | Tanigawa et al. | |
| 2012/0022373 | A1 | 1/2012 | Tateyama | |
| 2013/0286023 | A1* | 10/2013 | Friedman | A61B 8/08 345/440 |

FOREIGN PATENT DOCUMENTS

| | | |
|---|---|---|
| CN | 102449499 A | 5/2012 |
| JP | 2001-212144 A | 8/2001 |
| JP | 2007-296329 A | 11/2007 |
| JP | 2011-005237 A | 1/2011 |
| JP | 2011-224410 A | 11/2011 |
| WO | 2010/100868 A1 | 9/2010 |
| WO | 2012/035723 A1 | 3/2012 |

OTHER PUBLICATIONS

Hirofumi Taki, Kousuke Taki, Takuya Sakamoto, Makoto Yamakawa, Tsuyoshi Shiina and Toru Sato, High Range Resolution Medical Acoustic Vacular Imaging with Frequency Domain Interferometry, 2010 Annual International Conference of the IEEE Engineering in Medicine and Biology Society (EMBC), Buenos Aires, AR, Aug. 31, 2010-Sep. 4, 2010, 1: 5298-5301, IEEE, Piscataway NJ, 2005.

* cited by examiner

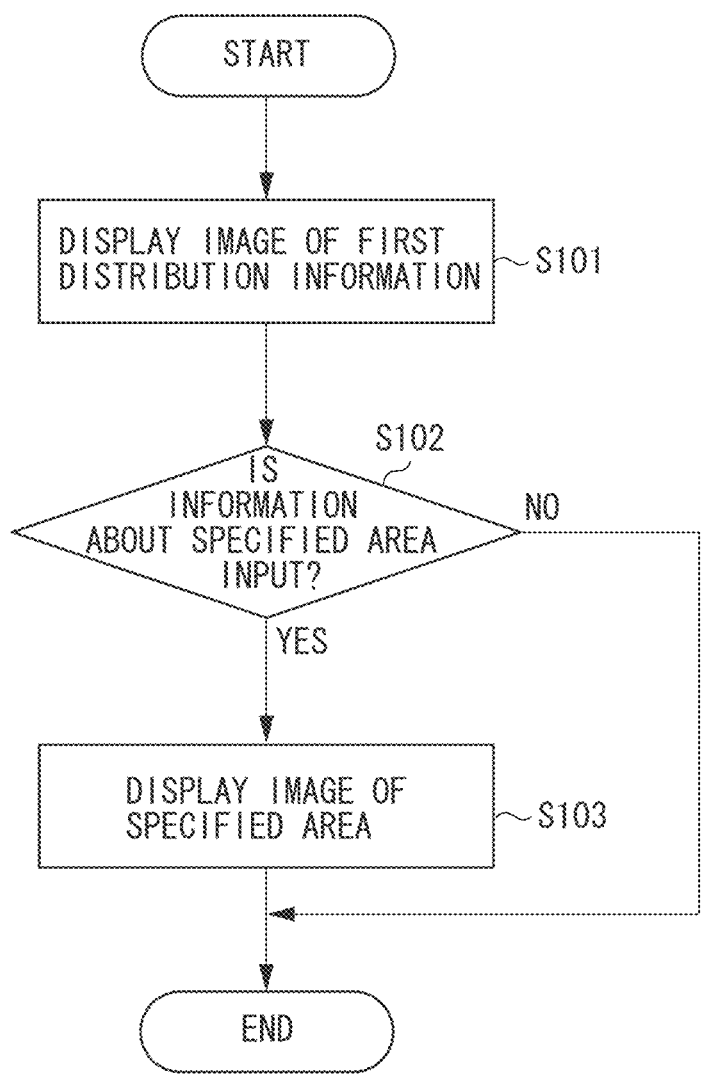

OBJECT INFORMATION OBTAINING APPARATUS, DISPLAY METHOD, AND STORAGE MEDIUM

BACKGROUND OF THE INVENTION

1. Field of the Invention

The present disclosure relates to an object information obtaining apparatus, a display method, and a storage medium. In particular, the present disclosure relates to a technique for displaying distribution information obtained by transmitting elastic waves to an object and receiving reflected waves from the object.

2. Description of the Related Art

In an ultrasonograph which is an object information obtaining apparatus, the spatial resolution in the depth direction in image data formation based on the pulse echo method can be generally represented by $(n\lambda)/2$, where $\lambda$ indicates the wavelength of ultrasonic waves and n indicates transmission wave number. For example, when the ultrasonograph transmits ultrasonic waves having a center frequency of 12 MHz for two wavelengths, the spatial resolution is about 0.13 mm.

The pulse echo method will be described below. When the ultrasonograph transmits ultrasonic wave pulses (elastic waves) to an object, the ultrasonic waves are reflected by the object according to the acoustic impedance difference inside the object, and return to the ultrasonograph. Then, the ultrasonograph receives the reflected waves and generates image data by using received signals of the reflected waves. Typically, the ultrasonograph obtains an envelope of the received signals, and converts the envelope into luminance values to generate image data. Repeating ultrasonic wave transmission and reception in a plurality of directions or positions inside the object enables obtaining luminance information on a plurality of scanning lines in the directions in which ultrasonic wave transmission and reception were made. Arranging the luminance information on the plurality of scanning lines enables imaging inside the object.

It is common that the ultrasonograph uses a plurality of conversion elements for converting the ultrasonic waves into electrical signals, and adds a temporal deviation to the received signal waveforms between each element, so that both transmission and reception are focused inside the object.

On the other hand, applying adaptive signal processing, which has developed in the field of the radar, together with ultrasonic waves enables improving the spatial resolution. Non patent document 1: M. SASSO et al., Medical Ultrasound Imaging Using The Fully Adaptive Beamformer, Proc. Acoustics, Speech Signal Process. volume. 2, pp. 489-492 (March 2005) discusses a technique using the Capon method (adaptive signal processing) to improve the spatial resolution in the direction perpendicular to the depth direction (direction perpendicular to the scanning line direction).

As a technique for improving the spatial resolution in the depth direction (scanning line direction), Non patent document 2: Hirofumi Taki, Kousuke Taki, Takuya Sakamoto, Makoto Yamakawa, Tsuyoshi Shiina and Toru Sato: Conf Proc IEEE Eng Med Biol Soc. 2010; 1: 5298-5301 discusses results of imaging of the layer structure of the blood vessel wall by applying the Frequency Domain Interferometry (FDI) method and the Capon method (adaptive signal processing). Applying the FDI method and the Capon method to received signals enables improving the spatial resolution in the depth direction. However, it is assumed that a plurality of reflective layers exists in a signal range (within a processing range) in the depth direction clipped for the FDI processing. A plurality of reflected waves from close reflective layers is highly likely to have high mutual correlations. It is known that applying adaptive signal processing, such as the Capon method, to received signals of a plurality of reflected waves having such high correlations will cause an unexpected operation, such as negating a desired signal. By using the frequency averaging technique to reduce (suppress) the effect by signals (correlated interference waves) having such correlations, the FDI method and the Capon method are applicable to the received signals of the reflected waves.

Applying adaptive signal processing, such as the Capon method or a method combining the FDI and Capon methods, enables improving the spatial resolution of images. However, if an image generated by such a new technique is displayed, a user (particularly, a doctor) may feel odd since the user is familiar with the conventional B mode image (an image produced by obtaining an envelope of a plurality of receiving signals, and converting the envelope into luminance values). In particularly, if only an image generated through adaptive signal processing is displayed, the odd feeling may increase.

SUMMARY OF THE INVENTION

An embodiment of the present invention is directed to providing a user-friendly display method and object information obtaining apparatus used when displaying an image generated through adaptive signal processing.

According to an aspect of an embodiment of the present invention, an object information obtaining apparatus includes a plurality of conversion elements configured to transmit elastic waves to an object, receive reflected waves reflected at respective positions inside the object, and convert the reflected waves into a plurality of receiving signals, a fixed signal processing unit configured to perform addition processing with a predetermined weight by using the plurality of receiving signals to obtaining first distribution information, an adaptive signal processing unit configured to perform adaptive signal processing with a weight adaptively changing according to the receiving signals by using the plurality of receiving signals to obtain second distribution information, and a display control unit to which the first distribution information and the second distribution information are input, and configured to output image information to be displayed on a display unit, wherein the display control unit is configured, upon reception of information about a specified area in the image of the first distribution information input by the user in a state where the image of the first distribution information is displayed, to output image information for displaying on the display unit an image of the second distribution information or a combined image for the first and second distribution information, corresponding to the specified area.

According to another aspect of the present invention, a display method displays an image on a display unit by using distribution information obtained by an object information obtaining apparatus, wherein the obtained distribution information includes first distribution information obtained by performing addition processing with a predetermined weight by using a plurality of receiving signals obtained by transmitting elastic waves to an object and receiving reflected waves reflected inside the object, and second distribution information obtained by performing adaptive signal processing with a weight adaptively changing according to the receiving signals by using the plurality of receiving signals, wherein the display method includes displaying the image of the first distribution information, and upon reception of information about a specified area in the image of the first distribution information input by the user, displaying the image of the second distribution information or the combined image for the first and second distribution information, corresponding to the specified image.

Further features and aspects of the present invention will become apparent from the following description of exemplary embodiments with reference to the attached drawings.

BRIEF DESCRIPTION OF THE DRAWINGS

FIG. 4 is a flowchart illustrating processing of a display method according to a first exemplary embodiment.

DESCRIPTION OF THE EMBODIMENTS

Figure 1:
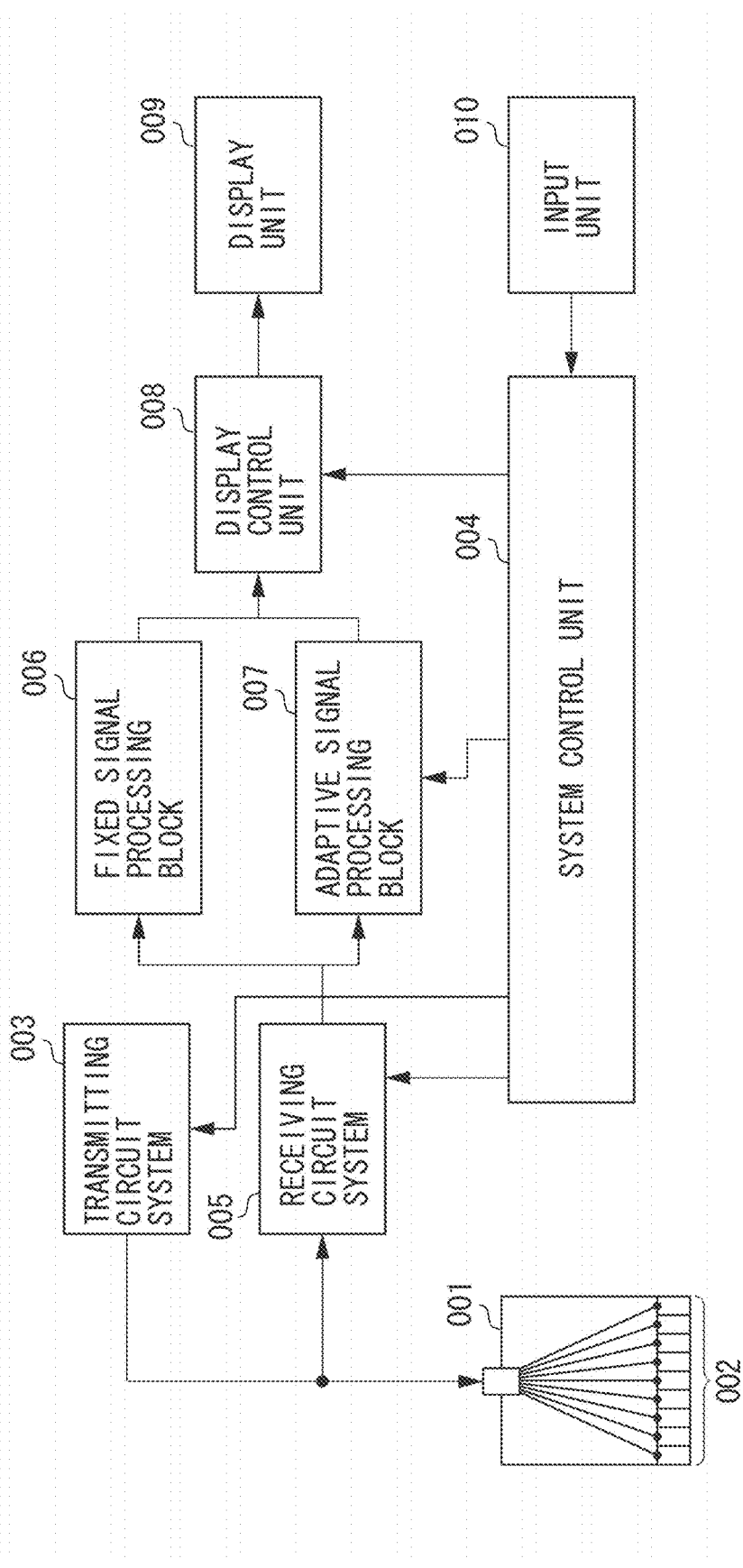
FIG. 1 schematically illustrates an overview of an object information obtaining apparatus according to the present invention.

Exemplary embodiments of the present invention will be described below with reference to the accompanying drawings. Basically, identical constitution elements are assigned the same reference numeral, and redundant descriptions will be omitted.

In an embodiment of the present invention, an elastic wave typically refers to an ultrasonic wave and includes sound wave, ultrasonic wave, or acoustic wave. The object information obtaining apparatus according to an embodiment of the present invention includes an apparatus which transmits elastic waves to an object, receives reflected waves (reflected elastic waves) reflected inside the object, and obtains distribution information inside the object as image data. The obtained distribution information inside the object is information reflecting the acoustic impedance difference between tissues inside the object. In an embodiment of the present invention, scanning lines indicate virtual lines formed in the traveling direction of elastic waves transmitted from a probe.

A first exemplary embodiment will be described below.

A basic apparatus configuration and processing flow will be described according to an embodiment of the present invention.

Basic Configuration of Object Information Acquisition Apparatus

A configuration of an object information obtaining apparatus according to the present exemplary embodiment of the present invention will be described below with reference to FIG. 1. FIG. 1 schematically illustrates an overview of the object information obtaining apparatus which can apply an embodiment of the present invention. The object information obtaining apparatus according to the present exemplary embodiment includes a probe 001 having a plurality of conversion elements 002, a receiving circuit system 005, a transmitting circuit system 003, a fixed signal processing block 006, an adaptive signal processing block 007, and a display control unit 008. The object information obtaining apparatus according to the present exemplary embodiment further includes a display unit 009, an input unit 010, and a system control unit 004.

The probe 001 is a receiver transmitter for transmitting elastic waves to a plurality of positions inside the object, and receives reflected waves. The probe 001 includes the plurality of conversion elements 002 for converting elastic waves into electrical signals.

The transmitting circuit system 003 is a transmission signal generation unit for generating, based on a control signal from the system control unit 004, a plurality of transmission signals having a delay time and an amplitude according to each target position and each target direction. The plurality of conversion elements 002 converts the transmission signals into elastic waves, and the probe 001 transmits the elastic waves to the object as elastic wave beams. The plurality of conversion elements 002 also receives elastic waves (reflected waves) reflected by target objects (reflecting interfaces and reflectors) inside the objects, and converts the elastic waves into a plurality of receiving signals. The receiving signals are input into the receiving circuit system 005.

The receiving circuit system 005 is a receiving signal processing unit for amplifying the plurality of receiving signals and converting the receiving signals into a plurality of digital signals (digitized receiving signals). In an embodiment of the present invention, not only analog receiving signals output by the conversion elements 002 but also amplified and digitally converted signals are referred to as receiving signals. The plurality of digital signals output from the receiving circuit system 005 are input into the fixed signal processing block 006 and the adaptive signal processing block 007.

Figure 2:
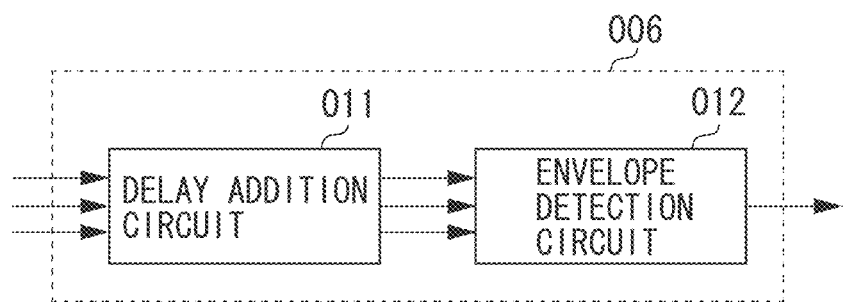
FIG. 2 schematically illustrates a configuration of a fixed signal processing block.

The fixed signal processing block 006 corresponds to a fixed signal processing unit according to an embodiment of the present invention. FIG. 2 illustrates a configuration of the fixed signal processing block 006. In the fixed signal processing block 006, a delay and sum circuit 011 (delay and sum unit) performs delay processing on the plurality of digital signals according to transmission directions and positions of the elastic waves, and then performs addition processing on the plurality of digital signals having undergone the delay processing. In other words, delay and sum processing is performed. A plurality of scanning line signals is obtained by the delay and sum processing. The fixed signal processing block 006 may multiply each of the plurality of digital signals by a weight before applying addition processing to the digital signals. Although the weight changes according to observation positions and transmission and reception conditions, a predetermined (fixed) weight is used in many cases. The delay and sum processing generates signals corresponding to the sound pressure of the reflected waves reflected at respective positions inside the object, as scanning line signals. Then, the envelope detection circuit 012 (envelope detection unit) performs envelope detection by the plurality of scanning line signals to obtain first distribution information. The fixed signal processing block 006 outputs the obtained first distribution information to the display control unit 008.

The adaptive signal processing block 007 corresponds to an adaptive signal processing unit according to an embodiment of the present invention. The adaptive signal processing adaptively changes relevant processing parameters according to the receiving signals. In particular, the Capon method (also referred to as Constrained Minimization of Power (CMP)), one of adaptive signal processing methods, performs processing on a plurality of input signals with sensitivity for the target directions and target positions being fixed state so that the electric power is minimized. Such adaptive signal processing has an effect of improving the spatial resolution. The adaptive signal processing block 007 outputs as second distribution information the power strength distribution having an improved resolution in at least one of the depth direction and the direction perpendicular to the depth direction. The depth direction refers to the traveling direction of the elastic waves (ultrasonic beams) transmitted from the probe 001, and equals the scanning line direction. Adaptive signal processing will be described in detail below with reference to FIGS. 3A, 3B, and 3C.

The first distribution information from the fixed signal processing block 006, and the second distribution information from the adaptive signal processing block 007 are input into the display control unit 008. The display control unit 008 outputs image information for displaying distribution information on the display unit 009. The display unit 009 displays an image indicating distribution information inside the object based on the image information output from the display control unit 008. The processing performed by the display control unit 008 will be described in detail below with reference to FIG. 4. The display control unit 008 performs various image processing, such as edge emphasis and contrast adjustment on image information of the first distribution information, image information of the second distribution information, and combined image information of the first and second distribution information, and outputs image information of luminance data.

In this exemplary embodiment, the fixed signal processing block 006, the adaptive signal processing block 007, the display control unit 008, and the system control unit 004 include processing devices such as a central processing unit (CPU), a graphics processing unit (GPU), and a field programmable gate array (FPGA) chip. The display unit 009 displays an image based on the image information input from the display control unit 008. The display unit 009 is configured with a liquid crystal display (LCD), a cathode ray tube (CRT), or an organic electroluminescence (EL) display.

The input unit 010 is used by a user to input a specified area. The user specifies a predetermined area by using the input unit 010, referring to an image of the first distribution information displayed on the display unit 009. The input unit 010 is configured with a pointing device, such as a mouse and a keyboard, a pen tablet, or a touchpad attached to the surface of the display unit 009. The display unit 009 and the input unit 010 may be connected to the object information obtaining apparatus according to an embodiment of the present invention, instead of being included in the object information obtaining apparatus according to an embodiment of the present invention.

Details of Adaptive Signal Processing

Figure 3A:
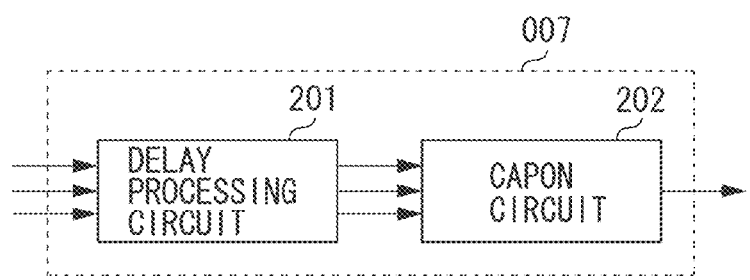
FIGS. 3A, 3B, and 3C schematically illustrate different configurations of an adaptive signal processing block.
Figure 3B:
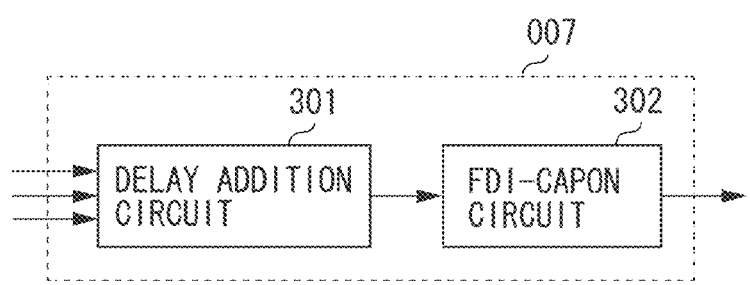
Figure 3C:
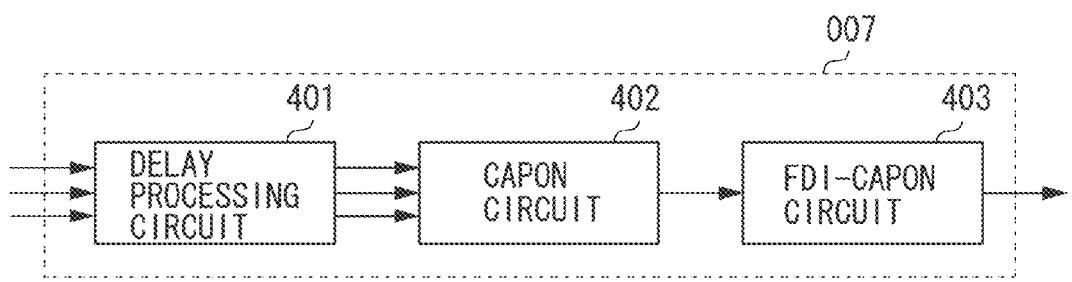

Processing performed by the adaptive signal processing block 007 of an embodiment of the present invention will be described below. FIGS. 3A, 3B, and 3C illustrate three different configurations of the adaptive signal processing block 007. Example configurations of the adaptive signal processing block 007 to which an embodiment of the present invention can be applied will be described below with reference to FIGS. 3A, 3B, and 3C.

FIG. 3A illustrates a configuration of the adaptive signal processing block 007 for improving the resolution in the direction perpendicular to the depth direction, i.e., the traveling direction of the elastic waves (ultrasonic beams) transmitted from the probe 001. Proc. Acoustics, Speech Signal Process. pp. 489-492 (March 2005) discusses a technique of such adaptive signal processing for improving the resolution in the direction perpendicular to the depth direction.

Processing performed when the adaptive signal processing is applied to the plurality of receiving signals will be described below based on the Capon method as an example.

Processing for calculating a correlation matrix based on the plurality of receiving signals will be described below. First, the delay processing circuit 201 performs the Hilbert transform and the delay processing (phasing processing) according to respective target positions on the plurality of receiving signals output from the plurality of conversion elements 002. The receiving signals in the complex representation are calculated in this way. When the s-th sample of a signal obtained by processing a receiving signal from the k-th element is xk[s], an input vector X[s] of the s-th sample is defined by the following formula.

$$X[s] = [x_1[s], x_2[s], \ldots , x_M[s]]^T \quad (1)$$

where M is a number of the element.

Then, a Capon circuit 202 (adaptive signal processing unit) calculates a correlation matrix $R_{xx}$ based on the input vector X[s].

$$R_{xx} = E[X[s]X^H[s]] = \begin{bmatrix} E[x_1[s]x_1^*[s]] & E[x_1[s]x_2^*[s]] & \ldots & E[x_1[s]x_M^*[s]] \\ E[x_2[s]x_1^*[s]] & E[x_2[s]x_2^*[s]] & \ldots & E[x_2[s]x_M^*[s]] \\ \vdots & \vdots & \ddots & \vdots \\ E[x_M[s]x_1^*[s]] & E[x_M[s]x_2^*[s]] & \ldots & E[x_M[s]x_M^*[s]] \end{bmatrix} \quad (2)$$

where the superscript H indicates a complex conjugate transposition, and the superscript * indicates a complex conjugate. E[•] indicates processing for calculating a time average, i.e., processing for varying the sample number (s in this case) and calculating an average.

Then, to suppress the effect of a correlated interference wave which reaches the probe 001 from other than target directions, the Capon circuit 202 performs the spatial averaging method on the correlation matrix $R_{xx}$ to obtain an average correlation matrix $R'_{xx}$.

$$R'_{xx} = \sum_{n=1}^{M-K+1} z_n R_{xx}^n \quad (3)$$

where $R''_{xx}$ indicates a partial matrix in the correlation matrix $R_{xx}$, moving along the diagonal elements of $R_{xx}$. Specifically, $R''_{xx}$ is a matrix having a size of K×K, positioned so that the (n, n) element of $R_{xx}$ equals the first diagonal element of $R''_{xx}$. $Z_n$ indicates a coefficient used when adding respective partial matrices, and is adjusted so that the sum total of $Z_n$ equals 1.

The Capon method obtains a complex weight for minimizing the output power under certain restriction conditions. The complex weight refers to a weight represented by a complex vector. With the Capon method, an optimum complex weight $W_{opt}$ for minimizing the output power, with the sensitivity for the receiving signals of the elastic waves from the target directions restrained to 1, can be calculated by the following formula.

$$W_{opt} = \gamma R'^{-1}_{xx} C, \gamma = \frac{1}{C^H R'^{-1}_{xx} C} \quad (4)$$

where C indicates a restriction vector which varies according to the element position and target direction. However, if the phasing delay processing has been performed on the receiving signals, C may be a vector in which all values are 1 in the size (K in this case) of the average correction matrix.

An electric power $P_{min}$ can be calculated as follows based on the complex weight $W_{opt}$. The calculated electric power $P_{min}$ indicates distribution information (information about distribution related to the acoustic characteristics) reflecting the acoustic impedance difference between tissues inside the object according to the present exemplary embodiment.

$$P_{min} = \frac{1}{2} \frac{1}{C^H R'^{-1}_{xx} C} \quad (5)$$

The Capon circuit 202 can obtain a correlation matrix and further an average correction matrix based on the receiving signals, and, by using an inverse matrix, obtain a complex weight and a power distribution by using the complex weight. The complex weight and the electric power by using the complex weight are a complex weight and an electric power when the sensitivity is set to 1 for signals of the elastic waves from the target directions, and signals of the elastic waves reaching from other directions are suppressed. In other words, the Capon method enables selectively extracting signals of the elastic waves from the target directions, resulting in an improved spatial resolution in the direction perpendicular to the depth direction.

The electric power can also be calculated by applying QR decomposition and backward substitution processing to the average correction matrix, without directly obtaining an inverse matrix. The adaptive signal processing block 007 performs the adaptive signal processing (using the Capon method) with a weight adaptively changing according to the receiving signals, by using the plurality of receiving signals in this way. As a result, the adaptive signal processing block 007 outputs a power strength distribution (corresponds to the second distribution information) having an improved spatial resolution in the direction perpendicular to the depth direction.

A second exemplary configuration of the adaptive signal processing block 007 will be described below with reference to FIG. 3B.

FIG. 3B illustrates a configuration of the adaptive signal processing block 007 for improving the resolution in the depth direction, i.e., the traveling direction of the elastic waves (ultrasonic beams) transmitted from the probe 001. As a technique for improving the spatial resolution in the depth direction, the adaptive signal processing is combined with the Frequency Domain Interferometry (FDI) method. Hirofumi Taki, Kousuke Taki, Takuya Sakamoto, Makoto Yamakawa, Tsuyoshi Shiina and Toru Sato: Conf Proc IEEE Eng Med Biol Soc. 2010; 1: 5298-5301 discusses a technique in which the FDI method and the Capon method (adaptive signal processing) are applied.

The FDI method decomposes the receiving signals into frequency components, and varies the phase of the decomposed signals according to the target positions to presume the received electric power at the target positions. Phase variation can be predetermined based on the product of the distance from a certain reference position to the target positions and the wave number corresponding to the frequency.

Specifically, a method combining the FDI method and adaptive signal processing will presume the received electric power at the target positions by applying change of phase and weight calculated for each signal through adaptive signal processing, instead of predetermined fixed change of phase and weight, to the receiving signals decomposed into frequency components.

When applying the frequency averaging technique to the receiving signals of the elastic waves having a wide frequency band as with pulse waves, whitening is desirably applied to the receiving signals based on a reference signal.

Referring to FIG. 3B, the delay and sum circuit 301 (delay and sum unit) performs the delay processing on the plurality of digital signals according to the transmission directions and positions of the elastic waves, and performs delay and sum on the plurality of digital signals having undergone the delay processing. In other words, the delay and sum processing is performed. Similar to the delay and sum in the fixed signal processing block 006, the delay and sum in the adaptive signal processing block 007 generates signals corresponding to the sound pressure of the reflected waves reflected at respective positions inside the object, as scanning line signals.

Then, an FDI-Capon circuit 302 (FDI adaptive processing unit) receives as input signals the plurality of scanning line signals output from the delay and sum circuit 301. Then, the FDI-Capon circuit 302 extracts signals for the time interval of one unit of processing, i.e., the processing range, based on the plurality of scanning line signals.

Then, the FDI-Capon circuit 302 performs the Fourier transform on the extracted signals to decompose the signals into frequency components ($X_{s1}, X_{s2}, X_{s3}, \ldots,$ and $X_{sN}$). In the meantime, at least one reference signal from a reference signal storage unit (not illustrated) is input into the FDI-Capon circuit 302. Then, the FDI-Capon circuit 302 performs the Fourier transform on the reference signal to decompose the reference signal into frequency components ($X_{r1}, X_{r2}, X_{r3}, \ldots, X_{rN}$).

Then, the FDI-Capon circuit 302 performs whitening represented by the following formula.

$$X_{wk} = \frac{X_{sk} X^*_{rk}}{|X_{rk}|^2 + \eta} \quad (6)$$

where $X_{wk}$ (k=1, 2, ..., N) indicates frequency components, $\eta$ indicates a minute amount for stabilization of calculation, and * indicates a complex conjugate, after whitening. Then, the FDI-Capon circuit 302 calculates a correlation matrix R by using a vector $X_f$ including frequency components that have undergone whitening.

$$X_f = [X_{W1}, X_{W2}, \ldots, X_{WN}]^T$$

$$R = X_f X_f^{T*}$$

where T indicates transposition. The correlation matrix R is a matrix having a size of N×N.

Then, the FDI-Capon circuit 302 extracts partial matrices from the correlation matrix R, and performs the frequency averaging technique on the partial matrices for averaging.

$$R' = \frac{1}{M}\sum_{m=1}^{M} R_m \qquad (7)$$

$$R_{mij} = X_{W(i+m-1)}X^*_{w(j+m-1)}$$

where R' indicates a frequency average correlation matrix, $R_m$ indicates a partial matrix of the correlation matrix R including $R_{mij}$ as elements. Thus, the FDI-Capon circuit 302 calculates the frequency average correlation matrix R'.

Then, the restriction vector C is input into the FDI-Capon circuit 302. The restriction vector C varies according to a position r within the processing range, and is defined by the following formula.

$$C = [\exp(jk_1 r), \exp(jk_2 r), \ldots, \exp(jk_{(N-M+1)} r)]$$

The FDI-Capon circuit 302 calculates a power strength distribution P(r) in the processing range based on the frequency average correction matrix R' and the restriction vector C. The calculated power strength distribution P(r) indicates distribution (distribution related to the acoustic characteristics) information reflecting the acoustic impedance difference between tissues inside of the object according to the present exemplary embodiment.

$$P(r) = \frac{1}{C^{T*}(R' + \eta' E)^{-1} C} \qquad (8)$$

where $\eta'E$ indicates a diagonal matrix added to stabilize the inverse matrix calculation.

In the present exemplary embodiment, the adaptive signal processing block 007 performs the FDI method and adaptive signal processing (based on the Capon method) by using the plurality of receiving signals in this way. As a result, the adaptive signal processing block 007 outputs a power strength distribution (corresponds to the second distribution information) with an improved resolution in the depth direction.

A third exemplary configuration of the adaptive signal processing block 007 will be described below with reference to FIG. 3C. A delay processing circuit 401 performs the Hilbert transform and the delay processing for respective target positions on the plurality of receiving signals output from the plurality of conversion elements 002, and outputs digital signals. A Capon circuit 402 performs the Capon processing on the digital signals that have undergone the delay processing as input. The Capon circuit 402 performs similar processing to the above-described processing (redundant descriptions will be omitted), and eventually outputs a signal Y[s] calculated by the following formula.

$$Y[s] = W_{opt}^H X'[s] \qquad (9)$$

where X'[s] indicates a vector extracted from the input vector X[s] of the s-th sample, fitting the size of the complex weight $W_{opt}$.

The output Y[s] holds phase information of the reflected waveforms according to target position, enabling performing subsequent FDI-Capon processing. The FDI-Capon circuit 302 performs the FDI-Capon processing on the input signal Y[s], and outputs a power strength distribution.

Performing such processing enables obtaining a power distribution with improved resolutions in the depth direction and in the direction perpendicular to the depth direction.

Although the processing of the Capon method has specifically been described as an example of adaptive signal processing, similar effects of an embodiment of the present invention can also be obtained by applying other adaptive signal processing, such as the MUltiple SIgnal Classification (MUSIC) method and the Estimation of Signal Parameters via Rotation Invariance Techniques (ESPRIT) method.

Display Method

Processing performed by a display method according to the present exemplary embodiment will be described below with reference to FIG. 4. FIG. 4 is a flowchart illustrating the display method according to the present exemplary embodiment.

In step S101, the display control unit 008 outputs to the display unit 009 image information for displaying the image of input first distribution information. The display unit 009 displays the image of the first distribution information based on the image information.

In step S102, the display control unit 008 determines whether information about the specified area (hereinafter referred to as specified area information) is input from the user. The user inputs an area (specified area) to be subjected to high-resolution image display by using the input unit 010, such as a mouse, while monitoring the image of the first distribution information displayed on the display unit 009. The specified area information is input into the system control unit 004 from the input unit 010, and the system control unit 004 outputs the specified area information to the display control unit 008. Thus, to input a specified area, the user specifies a desired area in the image of the first distribution information to complete the input of the specified area. Alternatively, a specified area application instruction may be input by the user inputting a specified area and then clicking the APPLY SPECIFIED AREA button (refer to FIG. 5) displayed on the screen of the display unit 009.

If specified area information is input (YES in step S102), then in step S103, the display control unit 008 displays the image of the second distribution information or the combined image for the first and second distribution information, at the position corresponding to the specified area. The present exemplary embodiment will be described below centering on a case where the image of the second distribution information at the position corresponding to the specified area is displayed. A case where the combined image for the first and second distribution information is displayed will be described in a third exemplary embodiment (described below).

Figure 5:
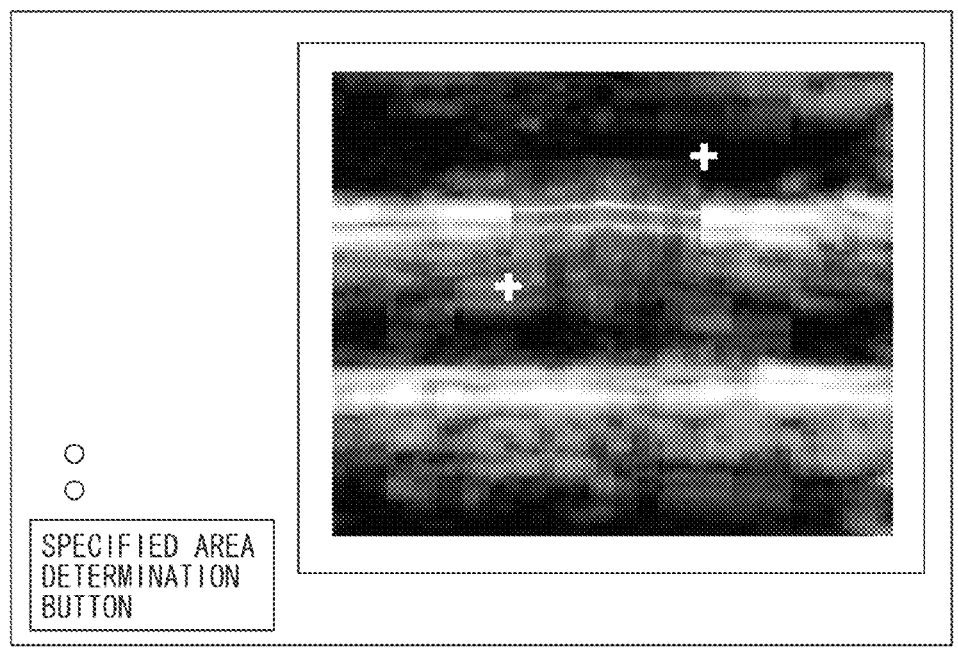
FIG. 5 illustrates an example screen displayed on a display unit according to the first exemplary embodiment.

FIG. 5 illustrates an example screen displayed on the display unit 009 according to the present exemplary embodiment. FIG. 5 illustrate the layer structure of the blood vessel wall. In the example illustrated in FIG. 5, the adaptive signal processing block 007 performs processing combining the FDI method and the Capon method (the example illustrated in FIG. 3B) as adaptive signal processing to obtain the image of the second distribution information.

In the example illustrated in FIG. 5, by using the input unit, such as a mouse, the user specifies two points by moving a cross-shaped guide displayed in the first distribution information, thus inputting a specified area.

The screen also displays the specified area determination button. If the user clicks the specified area determination button in a state where specified area input has completed (in a state where the specified area information has been input to the display control unit 008), an instruction for changing the specified area in the image of the first distribution information to the image of the second distribution information is input to the display control unit 008.

Referring to FIG. 5, an area above the center of the image of the first distribution information is the specified area.

Only the specified area displays the image of the second distribution information having a high resolution in the depth direction. Specifically, displayed image of the blood vessel wall is sharp only in the specified area.

As in the present exemplary embodiment, firstly displaying an overall image by using the image of the first distribution information enables reducing user's uncomfortable feeling. Subsequently displaying the high-resolution image of the second distribution information only for an area of interest enables in-depth observation of the layer structure of the blood vessel wall. Further, using the high-resolution image of the second distribution information, for example, enables more accurately measuring the thickness of the blood vessel wall.

In the present exemplary embodiment, the specified area can be moved. Specifically, the image of the second distribution information can be moved within the image of the first distribution information. In this case, the display control unit 008 outputs image information to the display unit 009 so that the image is displayed following the movement of the specified area, i.e., the image of the second distribution information at the position of the specified area after the movement is displayed.

The size of the specified area can also be changed. Specifically, the size of the image of the second distribution information can be changed within the image of the first distribution information. In this case, the display control unit 008 outputs image information to the display unit 009 so that the image is displayed to fit the changed size of the specified area, i.e., the image of the second distribution information within the specified area after the size change is displayed.

Referring to FIG. 5, a frame around entire circumference for emphasizing the boundary (a rectangle frame for indicating the specified area) is not displayed at the boundary between the image of the first distribution information and the image of the second distribution information. This is because providing no frame around entire circumference in the periphery of the area of user's interest may enable improving the visibility of the image.

Further, the guide according to the present embodiment may be not only the above described cross-shaped guide but also a linear-shaped guide. For example, a case in which processing combining the FDI method and the Capon method is performed as the adaptive signal processing to obtain the image of the second distribution information as illustrated in FIG. 5 is described. In this case, it is advantageous to display a guide indicating the boundary in a direction perpendicular to the depth direction (horizontal direction), and not to display a guide indicating the boundary in the depth direction (vertical direction).

This is because it is conceivable to involve a target in the form of laminae such as the blood vessel wall continuing in a direction perpendicular to the depth direction as an observation target since resolution in the depth direction is improved in the case of the processing combining the FDI method and the Capon method. Specifically, it can be prevented that the guide in the vertical direction buries a part of the target continuing in the horizontal direction.

Further, a case in which processing that improves resolution in a direction perpendicular to the depth direction (for example, performing only the Capon method) is performed as the adaptive signal processing to obtain the image of the second distribution information, it is advantageous to display a guide in a vertical direction, and not to display a guide in a horizontal direction.

However, in an embodiment of the present invention, processing is not limited to the above described examples, and a frame for indicating the specified area may be displayed as a guide. Providing such a guide for indicating the specified area has the advantage of making it easier for the user to perform operation to move the specified area and change the size thereof. Therefore, in the present exemplary embodiment, it is desirable that the user can selectively execute a mode in which the guide for indicating the specified area is displayed and a mode in which the relevant guide is not displayed. For example, the display screen may desirably include a button for turning display of the guide for indicating the specified area ON and OFF.

Although, in the present exemplary embodiment, only the image of the second distribution information is displayed in the specified area, the effect of an embodiment of the present invention can also be obtained by displaying the combine image for the first and second distribution information.

Furthermore, although, in the present exemplary embodiment, firstly the overall image is displayed by using the image of the first distribution information, and subsequently, the area of user's interest (specified area) is displayed by switching to the image of the second distribution information, the present exemplary embodiment may be performed in an opposite manner. Specifically, firstly the overall image may be displayed by using the image of the second distribution information, and subsequently, the specified area may be switched to the image of the first distribution information. In this example, the user first observes the target structure in detail by taking a look at the image of the second distribution information with high resolution. After that, the user takes a look at the conventional familiar image of the first distribution information. In such an example, the user can take a look at the both image to facilitate usability.

A second exemplary embodiment will be described below.

The present exemplary embodiment differs from the first exemplary embodiment in the screen displayed on the display unit 009. An object information obtaining apparatus according to the present exemplary embodiment has a similar configuration to that of the object information obtaining apparatus illustrated in FIG. 1. Since the overview of the display method is basically the same as the flow described with reference to FIG. 4, the following exclusively describes display processing different from that according to the first exemplary embodiment, with reference to FIG. 6.

In the present exemplary embodiment, when displaying the image of the second distribution information or the combined image for the first and second distribution information, at the position corresponding to the specified area in the image of the first distribution information, the image of the first distribution information and the image of the second distribution information are displayed on the same screen. However, the image of the second distribution information or the combined image for the first and second distribution information, corresponding to the specified area is displayed in another display area on the same screen as the screen displaying the image of the first distribution information.

Figure 6:
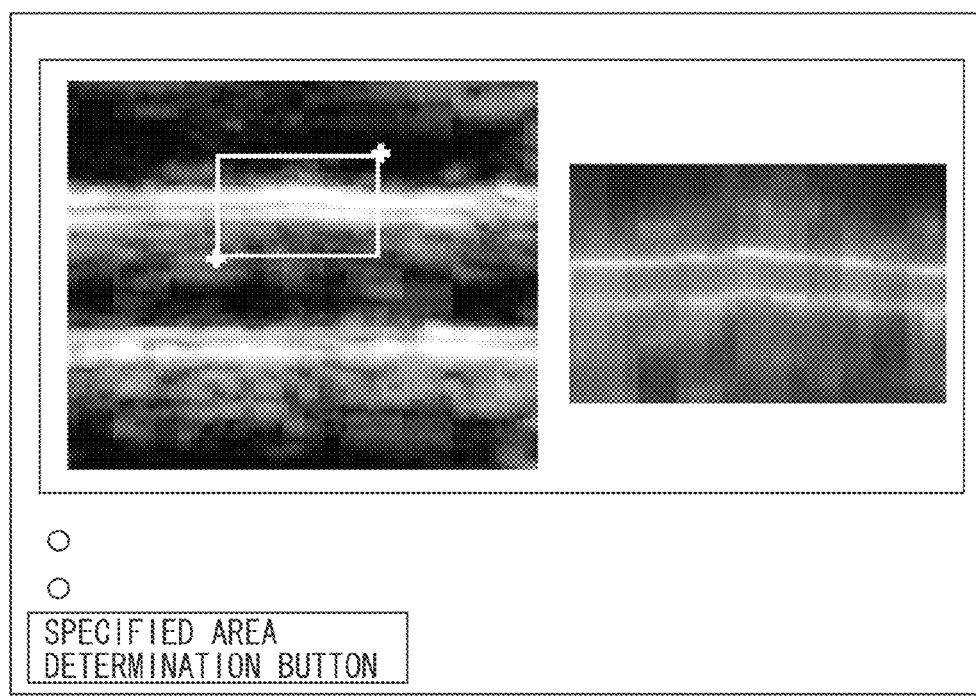
FIG. 6 illustrates an example screen displayed on the display unit according to a second exemplary embodiment.

FIG. 6 illustrate an example screen displayed on the display unit 009 according to the present exemplary embodiment. Referring to FIG. 6, the display control unit 008 also displays the image of the first distribution information in another display area in the screen displaying the image of the second distribution information at the position corresponding to the specified area. Similar to the first exemplary embodiment, the adaptive signal processing block 007 performs processing combining the FDI method and the Capon method (the example illustrated in FIG. 3B) as adaptive signal processing to obtain the image of the second distribution information.

Referring to FIG. 6, when displaying the image of the second distribution information in an area different from the area displaying the image of the first distribution information, the display control unit 008 displays an enlarged version of the image of the second distribution information. Thus, when displaying an enlarged version of the image of the second distribution information corresponding to the specified area, the user operation for specifying a desired area in the image of the first distribution information serves not only as a specified area input but also an enlargement instruction. Specifically, the display control unit 008 determines the enlargement rate of the enlarged image based on the relationship between the size of the specified area input by the user and the size of the display area of the display unit 009.

Displaying an enlarged version of the high-resolution image of the second distribution information only for the area of interest in this way enables in-depth observation of the layer structure of the blood vessel wall. Further, since the high-resolution image of the second distribution information is enlarged, the visibility is not easily degraded.

In the present exemplary embodiment, as illustrated in FIG. 6, the rectangle frame indicates the range of the specified area (indicated by the image of the second distribution information) in the image of the first distribution information. Displaying a guide for indicating the specified area, like this rectangle frame, makes it easier for the user to grasp the position in the image of the first distribution information corresponding to the high-resolution image. In the present exemplary embodiment, unlike the first exemplary embodiment, the image of the second distribution information is not combined in the image of the first distribution information. Therefore, even if the guide for indicating the specified area in the image of the first distribution information, the visibility is not easily degraded. However, also in the present exemplary embodiment, the user may be able to select a mode in which the guide for indicating the specified area is displayed and a mode in which the relevant guide is not displayed.

The position of the specified area can be moved by the user moving the guide for indicating the specified area. When the user inputs a guide movement instruction to the system control unit 004 via the input unit 010, the system control unit 004 outputs the guide movement information to the display control unit 008. Upon reception of the guide movement information, the display control unit 008 moves the guide on the screen, and displays on the display unit 009 the image of the second distribution information corresponding to the specified area after the movement.

The user can change the size of the specified area by changing the size of the guide for indicating the specified area. When the size of the specified area is changed, the enlargement rate of the image of the second distribution information is also changed. When a guide size change instruction is input from the user to the system control unit 004, the system control unit 004 outputs guide size change information to the display control unit 008. Upon reception of the guide size change information, the display control unit 008 changes the size of the guide on the screen, and displays on the display unit 009 the image of the second distribution information corresponding to the specified area after the size change.

Further, also in the present exemplary embodiment, firstly the overall image may be displayed by using the image of the second distribution information, and subsequently, the image of the first distribution information may be displayed as the image corresponding to the specified area.

A third exemplary embodiment will be described below.

The present exemplary embodiment is characterized in displaying, upon reception of information about a specified area in the image of the first distribution information, an enlarged version of the combined image for the first and second distribution information as the image corresponding to the specified area. Other processing is similar to that according to the first and second exemplary embodiments. An object information obtaining apparatus according to the present exemplary embodiment has a similar configuration to that of the object information obtaining apparatus illustrated in FIG. 1. Since the overview of the display method is basically the same as the processing described with reference to FIG. 4, the following exclusively describes display processing different from that according to the first and second exemplary embodiments.

In the present exemplary embodiment, upon reception of specified area information from the user, the display control unit 008 displays in step S103 (FIG. 4) the combined image for the first and second distribution information. The combination rate for the image of the first distribution information and the image of the second distribution information may be predetermined like 50:50, or arbitrarily set by the user. Further, as in the second exemplary embodiment, when displaying an enlarged version of the image of the specified area, the combination rate may be changed according to the enlargement rate.

Figure 7:
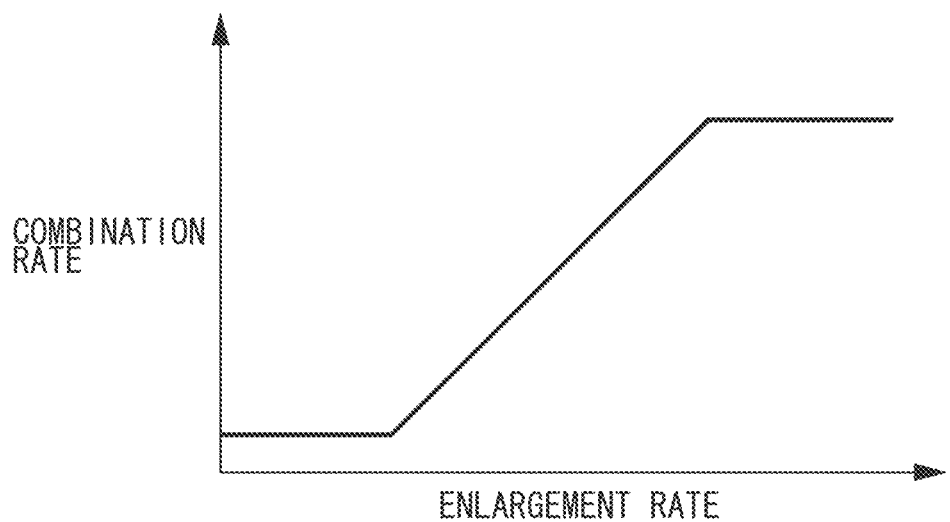
FIG. 7 illustrates a relationship between the enlargement rate and the combination rate according to a third exemplary embodiment.

FIG. 7 illustrates an example relationship between the enlargement rate and the combination rate. Referring to FIG. 7, when the enlargement rate is below a first predetermined value, the display control unit 008 maintains constant the combination rate for the first and second distribution information. In this case, because of a low enlargement rate, the combination rate (i.e., the ratio of the image of the first distribution information in the combined image) for the image of the second distribution information is high, and the ratio of the image of the second distribution information is low. Then, when the enlargement rate is higher than the first predetermined value and lower than a second predetermined value, the display control unit 008 increases the combination rate for the image of the second distribution information (the ratio of the image of the second distribution information to the image of the first distribution information in the combined image) with increasing enlargement rate. When the enlargement rate is equal to or higher than the second predetermined value, the display control unit 008 maintains constant the combination rate for the first and second distribution information. In this case, because of a high enlargement rate, the display control unit 008 increases the combination rate for the image of the second distribution information.

Changing the combination rate according to the enlargement rate in this way allows the user to more smoothly switching between the first and second distribution information without uncomfortable feeling, possibly improving the user operability.

A fourth exemplary embodiment will be described below.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-187617 filed Aug. 28, 2012 and Japanese Patent Application No. 2013-157608 filed Jul. 30, 2012, each of which is hereby incorporated by reference herein in its entirety.

What is claimed is:

1. An object information obtaining apparatus comprising:
a plurality of conversion elements configured to transmit elastic waves to an object, receive reflected waves reflected at respective positions inside the object, and convert the reflected waves into a plurality of receiving signals;
a fixed signal processing unit configured to perform addition processing with a predetermined weight by using the plurality of receiving signals to obtain first distribution information;
an adaptive signal processing unit configured to perform adaptive signal processing with a weight adaptively changing according to the receiving signals by using the plurality of receiving signals to obtain second distribution information; and
a display control unit to which the first distribution information and the second distribution information are input, and configured to output image information to be displayed on a display unit,
wherein the display control unit receives information about a specified area, in the image of the first distribution information, input by the user in a state where the image of the first distribution information is displayed, and outputs image information for displaying on the display unit an image of the second distribution information or a combined image for the first and second distribution information, corresponding to the specified area.

2. The object information obtaining apparatus according to claim 1, wherein, upon reception of the information about the specified area in the image of the first distribution information, the display control unit changes the image displayed in the specified area from the image of the first distribution information to the image of the second distribution information or the combined image.

3. The object information obtaining apparatus according to claim 2, wherein a position of the specified area displaying the image of the second distribution information or the combined image displayed in the specified area can be moved in the image of the first distribution information, and, following the movement, an image of the second distribution information or a combined image of the specified area at the position after the movement is displayed.

4. The object information obtaining apparatus according to claim 2, wherein the image of the second distribution information or the combined image displayed in the specified area can be changed in size in the image of the first distribution information, and, following the size change, the image of the second distribution information or the combined image in the specified area after size change is displayed.

5. The object information obtaining apparatus according to claim 1, wherein, upon reception of the information about the specified area in the image of the first distribution information, the display control unit displays in a display area different from the display area of the image of the first distribution information the image of the second distribution information or the combined image, corresponding to the specified area.

6. The object information obtaining apparatus according to claim 5, wherein, in a case where the image of the second distribution information or the combined image, corresponding to the specified area is displayed in the display area different from the display area of the image of the first distribution information, the display control unit displays a guide for indicating the position of the specified area in the image of the first distribution information.

7. The object information obtaining apparatus according to claim 5, wherein the display control unit displays in a display area different from the display area in the image of the first distribution information an enlarged version of the image of the second distribution information or the combined image, corresponding to the specified area.

8. The object information obtaining apparatus according to claim 6, wherein the guide is movable, and, following the movement of the guide, the image of the second distribution information or the combined image, at the moved position is displayed.

9. The object information obtaining apparatus according to claim 6, wherein the guide can be changed in size, and, following the size change of the guide, the image of the second distribution information or the combined image in the specified area after size change is displayed.

10. The object information obtaining apparatus according to claim 1, wherein the adaptive signal processing unit is configured to perform processing by using the plurality of reception signals with sensitivity for target directions being fixed state so that the electric power is minimized.

11. The object information obtaining apparatus according to claim 1, wherein the adaptive signal processing unit is configured to perform processing by using the plurality of reception signals with sensitivity for target positions in the depth direction being fixed state so that the electric power is minimized.

12. A display method for displaying an image on a display unit by using distribution information obtained by an object information obtaining apparatus, wherein the obtained distribution information includes
first distribution information obtained by performing addition processing with a predetermined weight by using a plurality of receiving signals obtained by transmitting elastic waves to an object and receiving reflected waves reflected inside the object, and
second distribution information obtained by performing adaptive signal processing with a weight adaptively changing according to the receiving signals by using the plurality of receiving signals, wherein the display method comprises:
displaying the image of the first distribution information; and
receiving information about a specified area, in the image of the first distribution information, input by the user, and displaying the image of the second distribution information or the combined image for the first and second distribution information, corresponding to the specified image.

13. The display method according to claim 12, wherein the displaying the image of the second distribution information or the combined image, corresponding to the specified area includes changing the image displayed in the specified area from the image of the first distribution information to the image of the second distribution information or the combined image.

14. The display method according to claim 13, wherein the image of the second distribution information or the combined image displayed in the specified area can be changed in size in the image of the first distribution information, and, following the size change, the image of the second distribution information or the combined image in the specified area after size change is displayed.

15. The display method according to claim 12, wherein the displaying the image of the second distribution information or the combined image, corresponding to the specified area includes displaying in a display area different from the display area of the image of the first distribution information the image of the second distribution information or the combined image, corresponding to the specified area.

16. The display method according to claim 15, wherein, in a case where the image of the second distribution information or the combined image, corresponding to the specified area is displayed in the display area different from the display area of the image of the first distribution information, a guide for indicating the position of the specified area is displayed in the image of the first distribution information.

17. The display method according to claim 15, wherein the displaying the image of the second distribution information or the combined image, corresponding to the specified area includes displaying in a display area different from the display area in the image of the first distribution information an enlarged version of the image of the second distribution information or the combined image, corresponding to the specified area.

18. The display method according to claim 16, wherein the guide is movable, and, following the movement of the guide, the image of the second distribution information or the combined image at the moved position is displayed.

19. The display method according to claim 16, wherein the guide can be changed in size, and, following the size change of the guide, the image of the second distribution information or the combined image in the specified area after size change is displayed.

20. A computer-readable storage medium storing program for causing a computer to execute the display method according to claim 12.

21. The object information obtaining apparatus according to claim 7, wherein in the case where the enlarged version of the combined image of the first and second distribution information is displayed, a combination ratio of the first and second distribution information is determined based on a size of the designated area.

22. The display method according to claim 12, further comprising displaying in a display area different from the display area in the image of the first distribution information an enlarged version of the image of the second distribution information or the combined image, corresponding to the specified area.

23. The display method according to claim 22, wherein in the case where the enlarged version of the combined image of the first and second distribution information is displayed, a combination ratio of the first and second distribution information is determined based on a size of the designated area.

24. A display method for displaying an image on a display unit by using distribution information obtained by an object information obtaining apparatus, wherein the obtained distribution information includes
first distribution information obtained by performing addition processing with a predetermined weight by using a plurality of receiving signals obtained by transmitting elastic waves to an object and receiving reflected waves reflected inside the object, and
second distribution information obtained by performing adaptive signal processing with a weight adaptively changing according to the receiving signals by using the plurality of receiving signals,
wherein the display method comprises:
displaying on the display, an image of one of an image of the first distribution information and an image of the second distribution information or a combined image of the first and second distribution images;
receiving a designation of an area within the image displayed on the display; and
displaying on the display, an image of the other of the image of the first distribution information and the image of the second distribution information or the combined image for the designated area.

25. The display method according to claim 24, wherein in the case where an enlarged version of the combined image of the first and second distribution information is displayed, a combination ratio of the first and second distribution information is determined based on a size of the designated area.

* * * * *